United States Patent
Momose et al.

[11] Patent Number: 5,173,928
[45] Date of Patent: Dec. 22, 1992

[54] TOMOGRAPH USING PHASE INFORMATION OF A SIGNAL BEAM HAVING TRANSMITTED THROUGH A TO-BE-INSPECTED OBJECT

[75] Inventors: Atsushi Momose, Saitama; Akira Fukuhara, Hachioji, both of Japan

[73] Assignee: Hitachi, Ltd., Tokyo, Japan

[21] Appl. No.: 725,451

[22] Filed: Jul. 3, 1991

[30] Foreign Application Priority Data

Jul. 9, 1990 [JP] Japan ................... 2-179667

[51] Int. Cl.⁵ ........................................... G01N 23/06
[52] U.S. Cl. ........................................ 378/4; 378/19; 378/145; 378/901; 378/62; 250/237 G; 364/413.14; 364/413.26
[58] Field of Search ............ 378/4, 901, 19, 145, 378/62; 364/413.13, 413.14, 400; 250/237 G; 356/345, 346, 351, 361

[56] References Cited

U.S. PATENT DOCUMENTS 4,340,304  7/1982  Massie ........................... 356/351
4,562,540  12/1985  Devaney ......................... 364/400

OTHER PUBLICATIONS

Applied Physics Letters, vol. 6, No. 8, Apr. 1965, pp. 155-156.

*Primary Examiner*—Janice A. Howell
*Assistant Examiner*—Kim-Kwok Chu
*Attorney, Agent, or Firm*—Fay, Sharpe, Beall, Fagan, Minnich & McKee

[57] ABSTRACT

A tomograph makes use of phase information obtainable from a radiation beam having transmitted a to-be-inspected object. In one embodiment, the tomograph has an interferometer for producing interference fringes between a signal beam having transmitted through the object and a reference beam and eventually producing Moiré fringes a detector for detecting the Moiré fringes, and a signal processing unit for processing outputs of the detector.

14 Claims, 7 Drawing Sheets

TOMOGRAPH USING PHASE INFORMATION OF A SIGNAL BEAM HAVING TRANSMITTED THROUGH A TO-BE-INSPECTED OBJECT

BACKGROUND OF THE INVENTION

The present invention relates to a tomograph for reconstructing a sectional radiograph or a tomogram of an object, from images of the object formed of radiation beams which have transmitted the object in a plurality of different directions, to inspect the inside of the object non-destructively, utilizing radiation such as X-rays, γ-rays and a neutron beam.

In the conventional tomography utilizing X-rays, γ-rays, or a neutron beam, images of a to-be-inspected object are formed of X-ray beams, γ-ray beams, or neutron beams which have passed through the to-be-inspected object in a plurality of different directions, and a tomogram of the object is obtained by performing an arithmetic operation with data on the transmission of the object to provide transmission images. Each of the transmission images according to the conventional tomography indicates the absorptivity of the object with respect to X-rays, γ-rays, or a neutron beam. Accordingly, the tomogram indicates the absorptivity distribution in a cross section of the object.

When a radiation beam such as an X-ray beam, a γ-ray beam, or a neutron beam transmits through an object, both the amplitude and the phase of the beam are changed. It has been known that a change in the phase is generally greater than a change in the amplitude for the transmission beam. Accordingly, when a tomogram is formed by using a change in the phase, this tomogram would be higher in the contrast than conventional tomogram which uses a change in the amplitude. The tomogram based upon a change in the phase indicates the refractive-index distribution in a cross section of the object. As a measuring technique in which a change in the phase is used, there exists phase-contrast microscopy. However, as far as the present inventors know, tomography for reconstructing a tomogram by measuring and using a change in the phase does not exist at present.

SUMMARY OF THE INVENTION

It is an object of the present invention to provide a tomograph utilizing an X-ray beam, a γ-ray beam or a neutron beam, in which a change in the phase of the beam is detected.

The tomograph according to the present invention provides a sectional radiograph or a tomogram having a high resolution obtained with the conventional tomography utilizing an X-ray beam, a γ-ray beam or a neutron beam and also having a higher contrast than that of the tomogram obtained with the conventional tomography.

According to one aspect of the present invention, the tomograph makes use of means for detecting a change in the phase of a radiation beam such as an X-ray beam, a γ-ray beam or a neutron beam caused at transmission by the radiation beam through a to-be-inspected object. The detection of the change in the phase of the radiation beam may be possible using an interference phenomenon of the radiation beam. Namely, a radiation beam is split into two beams propagating along two different paths, one of the beams transmitting through the object to form a signal beam, the other being not influenced by the object to form a reference beam. The signal beam and the reference beam are directed to interfere with each other to produce interference fringes, which provide phase information to be used for reproduction of an image of the object.

According to another aspect of the present invention, a tomograph of the type using phase information, comprises:

a radiation beam source for producing a radiation beam;

means for splitting the beam into first and second diffracted beams;

means for establishing first and second paths for the first and second diffracted beams intersecting each other, the establishing means being arranged to receive the first and second diffracted beams;

means for holding a to-be-inspected object on one of the first and second paths so that the diffracted beam propagating along the one path and transmitting through the object produces a signal beam while the other diffracted wave beam produces a reference beam, and interference fringes are generated in a space where the intersection takes place;

means arranged to be located in the space for producing Moiré fringes from the interference fringes; and means coupled to the Moiré fringe producing means for reproducing an image representative of the object.

In one embodiment of the present invention, the Bonse-Hart interferometer (that is, an X-ray interferometer proposed by Bonse and Hart and described on pp. 155–156 of the Appl. Phys. Lett., Vol. 6, No. 8, April 1965) may be employed to detect the phase of the beam having transmitted through a to-be-inspected object. The Bonse-Hart interferometer is cut out of a single crystal usually made of silicon so that three parallel thin crystal plates are left at regular intervals on a base portion. X-rays, γ-rays, or a neutron beam is diffracted from three crystal plates of the interferometer successively in the Laue case (that is, in such a manner that a wave reflected and diffracted from a crystal plate propagates in a direction capable of penetrating the crystal plate). In more detail, an incident beam is split into two beams propagating along different paths by the first crystal plate which is called "a beam splitter", and two beams are diffracted by the second crystal plate so that the diffracted beams interfere with each other and produce interference fringes on the third crystal plate. The second crystal plate and the third crystal plate are called "a mirror" and "an analyzer", respectively. The distance between adjacent ones of the interference fringes is equal to the lattice constant of the single crystal.

When an object to be inspected is disposed between the second crystal plate and the third crystal plate so that one of the two diffracted beams passes through or transmits the object, the phase of the beam having passed through the object is shifted, and thus positions of the interference fringes change a little. It is, however, impossible to observe the interference fringes and the shift directly, because the distance between adjacent ones of the interference fringes is as small as the lattice constant of the single crystal used, that is, several angstroms. When the interference fringes pass through the analyzer, the interference fringes and the crystal lattice of the analyzer overlap, and thus Moiré fringes are formed. The Moiré fringes include information on a phase shift of the X-ray beam, γ-ray beam or neutron beam. The phase information is taken out of the Moiré fringes by utilizing amplitude information, by inserting a phase shifter on the propagation path for one of the two beams, or by moving the analyzer in a direction of the diffraction vector.

In the first method utilizing amplitude information, the reference beam is selectively blocked to provide an image indicative of an absorptivity distribution in the to-be-inspected object and an image (that is, Moiré fringes) of the object having information on a phase distribution. An image indicative of the phase-shift distribution can be calculated from the intensity distributions in both of the above images.

In the second method using a phase shifter, the phase shifter is inserted in the propagation path for one of the signal beam and the reference beam, and the displacement of the Moiré fringes is detected while changing the thickness of the phase shifter as measured in a direction of the propagation path. Without the phase shifter, the Moiré fringes appear at positions where a phase shift is an integral multiple of $2\pi$. Accordingly, the phase-shift distribution can be known from the positions of the Moiré fringes. The phase of the beam, however, cannot be determined exactly at positions between adjacent ones of the Moiré fringes. When the phase shifter is placed on the beam propagation path to move the Moiré fringes, a phase shift at the positions of the moved Moiré fringes can be known. Thus, a wedge-shaped phase-shifter may be used, because the nominal thickness of the phase shifter is changeable by displacing the wedge-shaped phase shifter in a direction traversing the propagation path so that the distance the beam transmits through the phase shifter is changed. A means is, therefore, provided for displacing the phase shifter in a direction traversing or perpendicular to the propagation path.

In the second method, in order to move the Moiré fringes, the analyzer may be moved in the direction of the diffraction vector. In this case, the analyzer may be moved by a piezoelectric element, for example. In more detail, the analyzer is not detached from the interferometer, but a cut is formed in a part of the base portion of the interferometer to enable the analyzer to move by a very small distance. The distance of movement of the analyzer may be monitored in such a manner that a mirror is attached to the analyzer and the fine displacement of the mirror is directly read by a laser interferometer. Otherwise, the distance of movement of the analyzer may be monitored by utilizing the fact that the intensity of an X-ray beam, $\gamma$-ray beam, or neutron beam having passed through the analyzer varies in accordance with the movement of the analyzer.

As mentioned above, when a radiation beam such as an X-ray beam, a $\gamma$-ray beam, or a neutron beam transmits or passes through an object, both of the amplitude and phase of the beam are changed. A change in the amplitude (that is, attenuation of the beam) depends upon the absorptivity of the object, and a change in the phase depends upon the refractive index of the object. It has been known that the change in the phase is generally greater than the change in the amplitude. A phase-contrast tomograph according to the present invention detects the change in phase, and can reconstruct a tomogram higher in contrast than a tomogram reconstructed by the conventional tomograph using the change in the amplitude (that is, absorption of the beam by the object). Although the tomogram reconstructed by the conventional tomography indicates the absorptivity distribution in a cross section of the object, the tomogram reconstructed by the phase-contrast tomograph according to the present invention indicates the refractive-index distribution in a cross section of the object. The phase-contrast tomograph can additionally provide a tomogram indicative of absorptivity distribution by blocking the reference wave. Further, a three-dimensional image may be obtained by combining a multiplicity of tomograms indicative of different cross sections. Additionally, when an X-ray beam, a $\gamma$-ray beam, or a neutron beam passes through an object, the propagation path of the beam is bent a little because of reflection. The resolution of a tomogram obtained by the present invention may be basically limited by this phenomenon.

The present invention is particularly useful for inspecting an element distribution or a density distribution in an organic material or a living body.

DESCRIPTION OF THE PREFERRED EMBODIMENTS

Embodiments of a phase-contrast tomograph according to the present invention will be explained below, with reference to the drawings. Although the embodiments show a case where an X-ray beam is used, the embodiments are applicable to a case where a $\gamma$-ray beam or a neutron beam is used.

EMBODIMENT I

Figure 1:
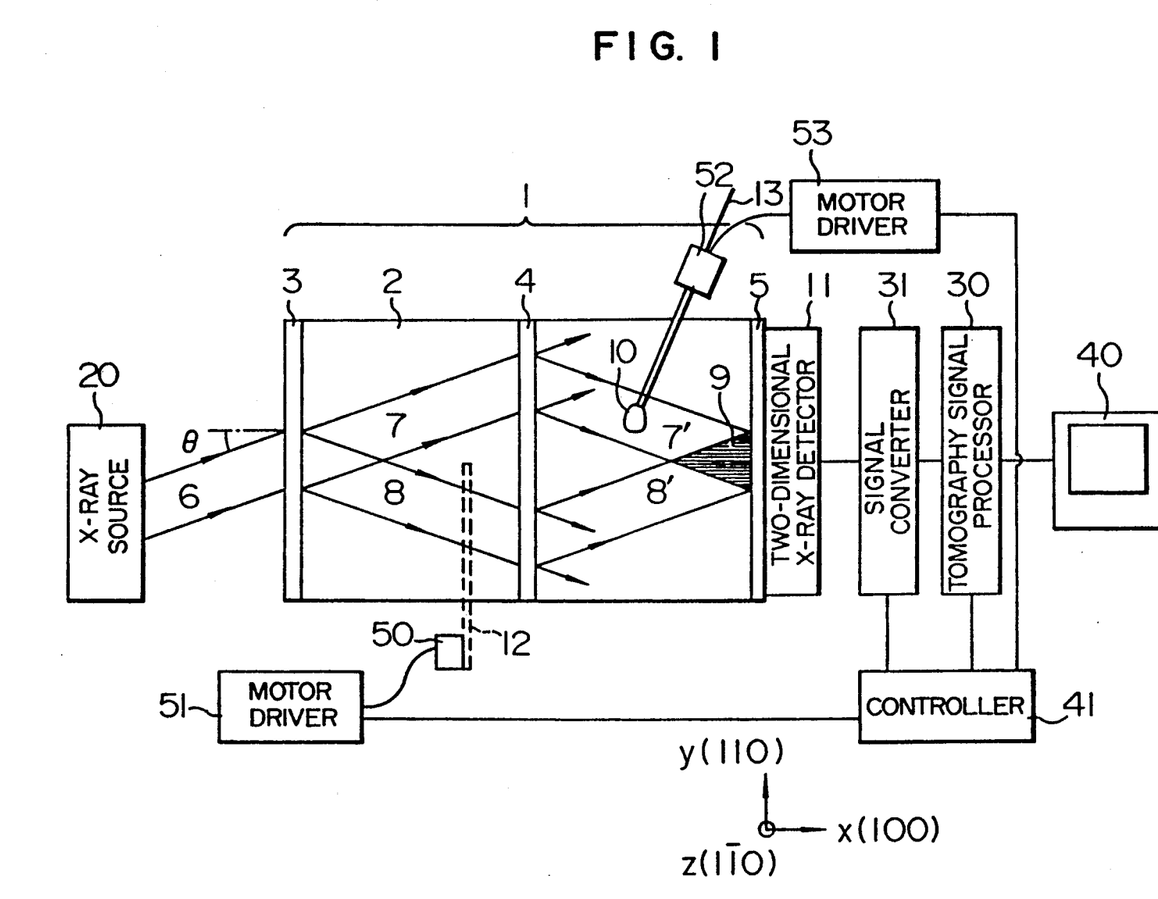
FIG. 1 is a schematic diagram showing a tomograph according to one embodiment of the present invention.

FIG. 1 shows a construction of a first embodiment of a phase-contrast tomograph according to an embodiment of the present invention. As shown in FIG. 1, the first embodiment includes an X-ray source 20, a Bonse-Hart X-ray interferometer 1 (indicated in a plan view), a two-dimensional X-ray detector 11, a shutter 12, a signal converter 31, a tomography signal processor 30, a controller 41 and a display device 40. A tomography signal process included in the conventional tomograph may be used as the tomography signal processor 30, as it is. In FIG. 1, the two-dimensional X-ray detector 11 is arranged so as to contact an analyzer 5 of the interferometer 1. The X-ray detector 11, however, may be spaced a distance from the analyzer 5 in any of the following embodiments, provided that the space distance of the X-ray detector 11 is equal to or greater than a value $1/\cos\theta$ (where 1 indicates the width of an X-ray beam, and $\theta$ indicates an incident angle of the X-ray beam into the beam splitter 3).

The Bonse-Hart X-ray interferometer 1 is cut out of a single crystal of silicon, and includes a sufficiently thick base portion 2, a beam splitter 3, a mirror 4, and the analyzer 5. The orientation of the crystal is chosen as shown in FIG. 1. That is, an X-axis, a Y-axis and a Z-axis are indicated by $<1, 0, 0>$, $<1, 1, 0>$ and $<1, -1, 0>$, respectively. Further, each of the beam splitter 3, the mirror 4 and the analyzer 5 has a thickness of 1 mm. The distance between the beam splitter 3 and the mirror 4 and the distance between the mirror 4 and the analyzer 5 are both made equal to 15 mm. X-rays are diffracted at (2, 2, 0) planes of the crystal in the Laue case.

A monochromatic X-ray beam from the X-ray source 20 is incident on the beam splitter 2 at an incident angle satisfying the Bragg condition, to be split into two diffracted beams 7 and 8. These beams are diffracted by the mirror 4, to be used as a signal beam 7' and a reference beam 8', respectively. The signal beam 7' and the reference beam 8' overlap and interfere with each other. Thus, interference fringes 9 are produced which have a period equal to the period $d_{220}$ of (2, 2, 0) planes of the crystal (for example, the period $d_{220}$ of silicon crystal is about 1.9 Å).

In more detail, the interference fringes 9 parallel to (2, 2, 0) planes of the crystal are produced at the analyzer 5. When the to-be-inspected object 10 is placed on the propagation path of the signal 7', the phase of the signal beam 7' changes, and accordingly, the interference fringes 9 move. That is, a phase shift due to the object 10 can be known by studying the interference fringes 10.

However, it is impossible to observe the interference fringes 9 directly, because the distance between adjacent ones of the interference fringes 9 is too small. When the interference fringes 9 pass through the analyzer 5, the interference fringes 9 and (2, 2, 0) planes of the analyzer 5 overlap, and thus Moiré fringes can be observed at the position of the two-dimensional X-ray detector 11. The Moiré fringes are detected and converted into an electric signal by the X-ray detector 11. The electric signal is sent to the signal converter 31. In the signal converter 31, an image indicative of the Moiré fringes is converted into an image indicative of a phase shift on the basis of the following principle. This signal conversion processing is carried out each time the body 10 is rotated by a body rotating motor 52 (driven by the motor driver 53) through a predetermined constant angle (for example, 1°), untill the body is rotated through an angle of 180°. The output of the signal converter 31 is sent to the tomography signal processor 30, in which a tomogram is reconstructed. The tomogram thus obtained is displayed on the display screen of the display device 40.

Operation procedures carried out by the signal processor 31 will be described below.

The interference fringes 9 are given by the following equation:

$$E(r) = A(r)exp(ik' \cdot r) + exp(ik \cdot r) \tag{1}$$

The first and second terms on the right-hand side indicate the signal beam and the reference beam, respectively. Further, in equation (1), r indicates a position vector, k the wave number vector of the reference beam, k' the wave number vector of the signal beam, i the unit of an imaginary number, and A(r) a change in the signal beam when the signal wave beam transmits or passes through the object 10. The factor A(r) is given in the form of a complex number, and the absolute value and argument of A(r) indicate a change in the amplitude (that is, absorption) and a change in the phase, respectively. In the present invention, the argument of the complex number A(r) is finally necessary, and a sectional radiograph or a tomogram is formed by using this argument. Assuming that a complex refractive index n of the object is represented by $n = 1 - \delta - i\beta$, the absolute value of A(r) will be expressed as $e^{-2\pi\beta t/\lambda}$, and the argument by $2\pi\delta(t/\lambda)$, where t denotes a distance the X-ray beam transmits through the object 10 and is variable depending on the location of the portion of the object 10 through which the beam transmits.

When the interference fringes 9 pass through the analyzer 5, Moiré fringes are observed at the position of the two-dimensional X-ray detector 11. Expressing the back surface of the analyzer 5 or the X-ray receiving surface of the detector 11 by a y-z coordinate system (the analyzer 5 being arranged so as to be contacted with the detector 11), then, the intensity distribution I(y, z) of the Moiré fringes is given by the following equation:

$$I(y, z) = W(y)|E(0, y, z)|^2 \tag{2}$$

where W(y) is a periodic function having a period of $d_{220}$ for indicating the transmittivity distribution of the analyzer.

Now, expressing the factor A(r) at the surface of the analyzer 5 by an amplitude $A_0(y, z)$ and an argument, that is, a phase shift $\phi(y, z)$, given the following equation:

$$A(0, y, z) = A_0(y, z)exp\{i\phi(y, z)\} \tag{3}$$

Then, by using equation (1), equation (2) can be rewritten as follows:

$$I(y, z) = W(y) [\{A_0(y, z)\}^2 + 1 + 2A_0(y, z) \cos\{\phi(y, z) + 2 y/d_{220}\}] \tag{4}$$

That is, when the amplitude $A_0(y, z)$ and the periodic function W(y) are known, the phase shift $\phi(y, z)$ is determined.

The periodic function W(y) is determined by using a standard sample, the complex refractive index of which is known. The complex refractive index of an object for X-rays is determined from the reflectivity and transmittivity of the object. Thus, a homogeneous object whose complex refractive index is previously determined, is machined to the shape of a wedge, to be used as the standard sample. The factors $A_{0m}(y, z)$ and $\phi_m(y, z)$ of the standard sample can be calculated from the shape thereof. Accordingly, placing the standard sample in the propagation path and measuring the intensity distribution $I_m(y, z)$ for the standard sample, the periodic function W(y) is determined using equation (4). It is to be noted that a symbol having a suffix m indicates a value for the standard sample.

Next, considering a case where the reference beam 8' is blocked by the shutter 12 (driven by the motor driver 51) and the object 10 is placed in the propagation path for the signal beam 7', the second term on the right-hand size of equation (1) is zero, and therefore the intensity distribution $I'(y, z)$ corresponding to equation (4) is given as follows:

$$I'(y, z) = W(y)\{A_0(y, z)\}^2 \quad (5)$$

Thus, the amplitude $A_0(y, z)$ of the object 10 is determined by using the periodic function $W(y)$ which has been determined by using the standard sample. Accordingly, the phase-shift distribution $\phi(y, z)$ can be determined from equation (4), because $W(y)$ and $A_0(y, z)$ are known.

Figure 2A:
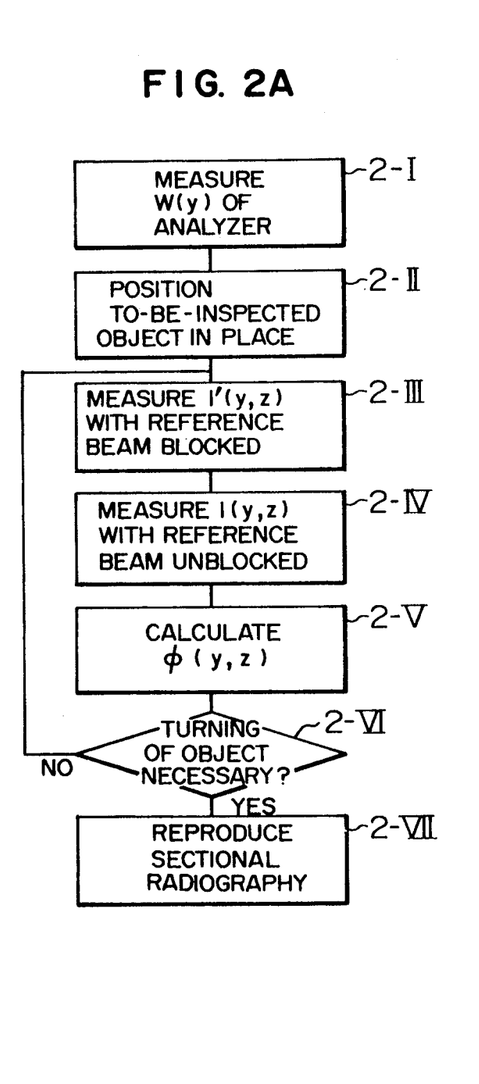
FIG. 2A is a flow chart showing steps for obtaining a tomogram indicative of refractive-index distribution, using the apparatus shown in FIG. 1.

FIG. 2A shows processing to be carried out by the first embodiment, for obtaining a tomogram of the object 10 indicative of the refractive index distribution. In step 2-I, the periodic function $W(y)$ indicative of the transmittivity of the analyzer 5 is determined by using a standard sample. In more detail, a homogeneous object, whose refractive index for X-rays has been previously measured, is machined to the shape of a wedge to be used as the standard sample. The standard sample is placed in the propagation path for the signal beam and the intensity distribution $I_m(y, z)$ of Moiré fringes is measured. Further, the amplitude $A_{0m}(y, z)$ and the phase shift $\phi_m(y, z)$ are calculated from the shape of the standard sample. Then, by using data $I_m(y, z)$, $A_{0m}(y, z)$ and $\phi_m(y, z)$, the periodic function $W(y)$ is determined using equation (4).

In step 2-II, the to-be-inspected object 10 is set in the propagation path for the signal beam 7'.

In step 2-III, the shutter 12 is set so as to block the reference beam 8', and the intensity distribution $I'(y, z)$ is measured by the two-dimensional X-ray detector 11.

In step 2-IV, the shutter 12 is withdrawn from the propagation path for the reference beam 8', and the intensity distribution $I(y, z)$ of Moiré fringes is measured by the two-dimensional X-ray detector 11.

In step 2-V, the amplitude $A_0(y, z)$ is determined from equation (5) by using data $W(y)$ and $I'(y, z)$, and the phase shift $\phi(y, z)$ is determined from equation (4) by using data $W(y)$, $A_0(y, z)$ and $I(y, z)$.

Then, the object 10 is rotated through a predetermined constant angle (for example, 1°), and the processing steps 3 to 5 are repeated. Further, this repetition is continued untill the object 10 is rotated through an angle of 180°. The phase shift $\phi(y, z)$ is determined at each rotational position of the body, that is, in each of the projective directions (step 2-VI).

In step 2-VII, data $\phi(y, z)$ thus obtained is sent to the tomography signal processor 31 to reconstruct a tomogram of the object, and the tomogram is displayed on the display screen of the display device 40.

Figure 2B:
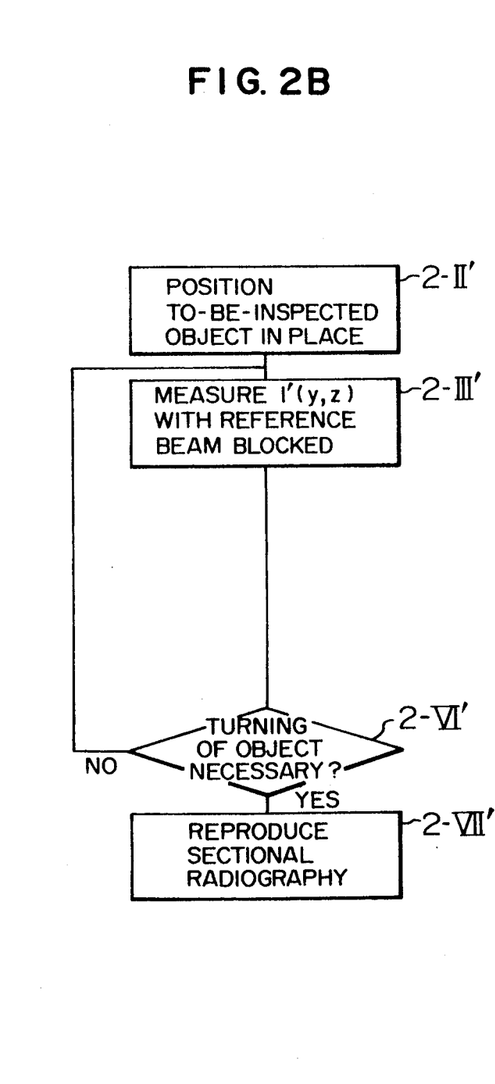
FIG. 2B is a flow chart showing steps for obtaining a tomogram indicative of absorptivity distribution, using the apparatus shown in FIG. 1.

FIG. 2B shows a procedure for obtaining a tomogram indicative of the absorptvity distribution in the object 10. In this case, the tomogram can be reconstructed directly from the intensity distribution $I'(y, z)$ obtained in step 2-III', by the processing in step 2-VII'. The processing in each of the steps 2-VII and 2-VII' is identical with processing in the conventional tomography for reconstructing a tomogram from transmission images. The controller 41 controls operations of the signal converter 31, motor driver 51 and motor driver 53. The controller 41 and the signal converter 31 may be realized by a computer.

EMBODIMENT II

Figure 3:
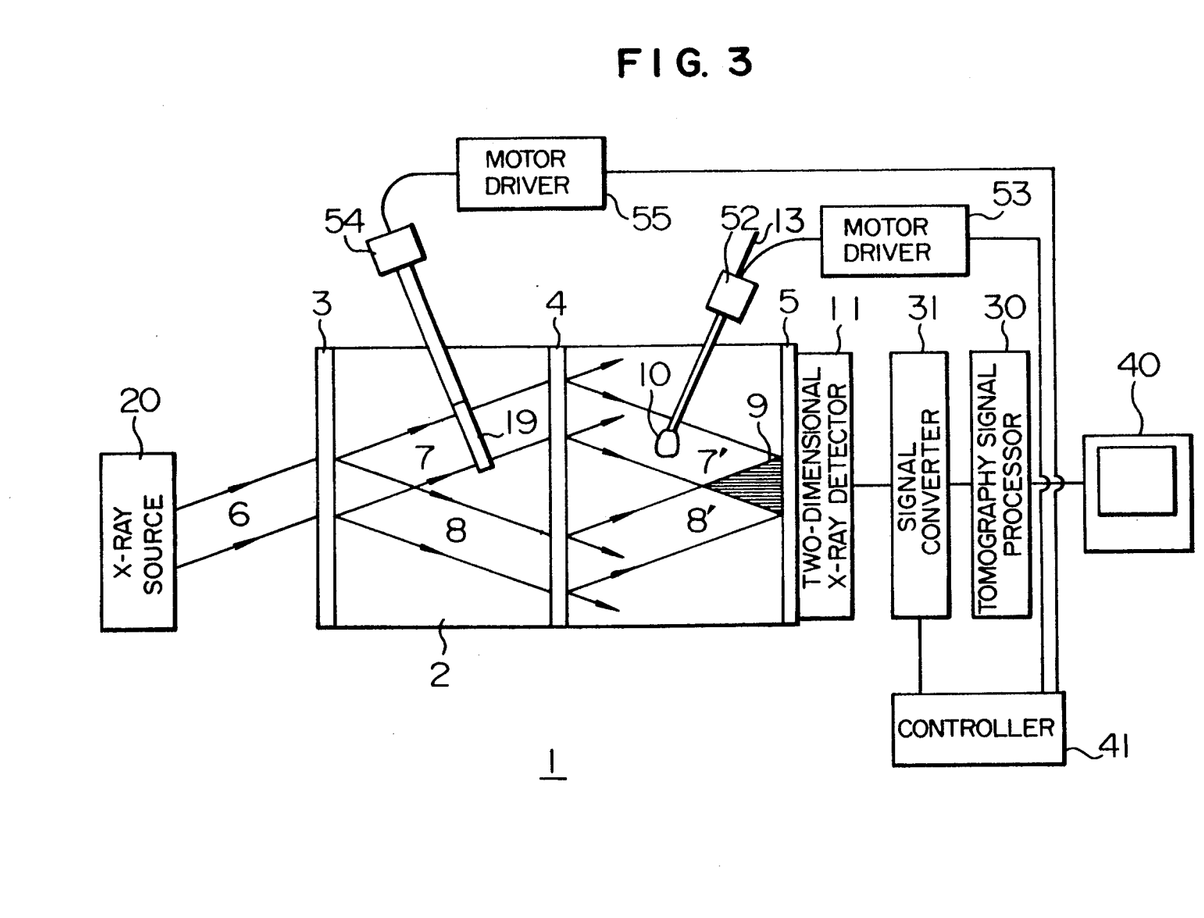
FIG. 3 is a schematic diagram of a tomograph according to another embodiment of the present invention.
Figure 4:
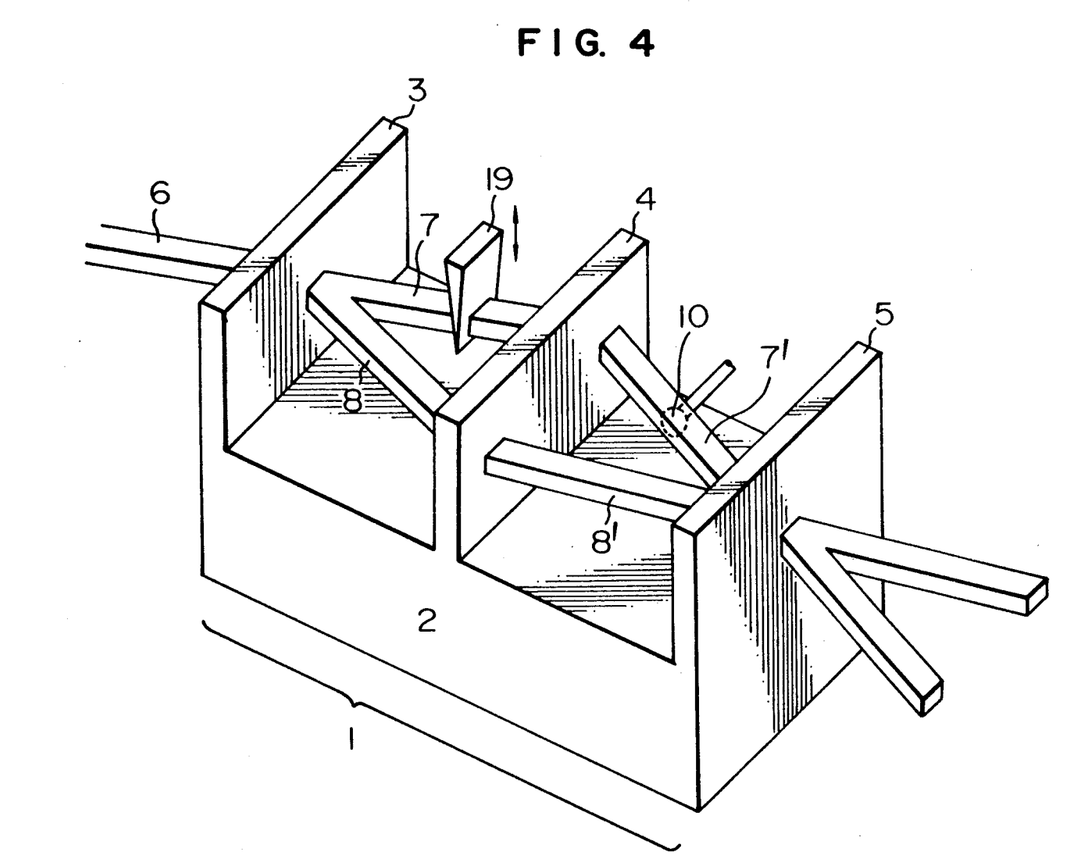
FIG. 4 is an enlarged view of the main part of the interferometer used in the embodiment shown in FIG. 3.

FIG. 3 shows a main part of a phase-contrast tomograph according to a second embodiment of the present invention. As shown in FIG. 3, the interferometer 1 used in the present embodiment is the same as that used in the first embodiment. FIG. 4 is a perspective view of the interferometer 1 shown in FIG. 3. It is to be noted that parts of the interferometer 1 other than a phase shifter 19 are omitted from FIG. 4.

As can be seen from equation (4), the Moiré fringes appear at intervals of a phase angle of $2\pi$. Accordingly, even when the amplitude $A_0(y, z)$ is unknown, it is known that the phase shift $\phi(y, z)$ at the positions of the Moiré fringes, that is, at positions having a maximum intensity, is $2n\pi$ (where n is an integer). In order to reconstruct the tomogram, it is required to determine the phase shift $\phi(y, z)$ at all of the coordinate values (y, z). That is, it is necessary to know the phase shift $\phi(y, z)$ at a position between adjacent ones of the Moiré fringes. A method of determining the phase shift $\phi(y, z)$ without using the amplitude $A_0(y, z)$ will be explained below.

Figure 5A:
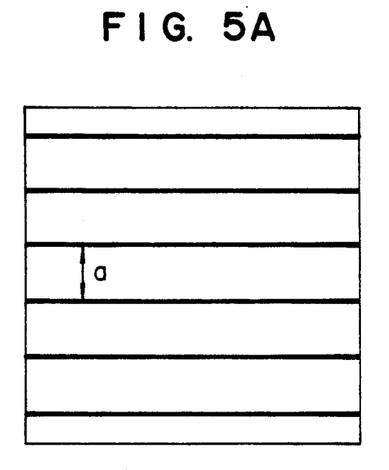
FIGS. 5A to 5D show examples of Moiré fringes observed with the apparatus shown in FIG. 3.
Figure 5B:
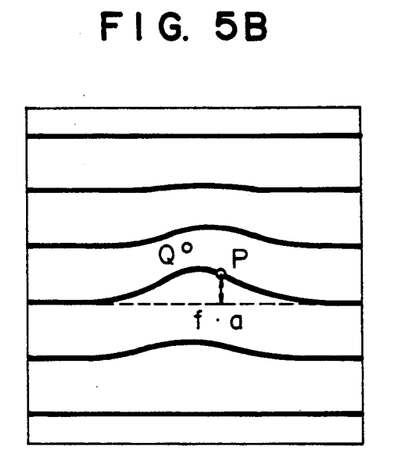

Now, let us consider a case where a phase shifter having the form of a wedge is placed in the propagation path for at least one of the signal wave beam and the reference wave beam. In FIG. 3, the phase shifter 19 having the form of wedge is movably placed in the propagation path for the signal beam. The phase shifter 19 is moved by a motor 54 driven by a motor driver 55. FIGS. 5A to 5D show examples of Moiré fringes obtained with the detector 11. In more detail, FIG. 5A shows Moiré fringes obtained in the absence of the object 10, and FIG. 5B shows Moiré fringes obtained with the object 10 placed in the propagation path for the signal beam. Thus, the phase shift $\phi(y, z)$ can be detected as the deviation of the Moiré fringes of FIG. 5B from the Moiré fringes of FIG. 5A.

Now, defining the distance between adjacent ones of Moiré fringes by a, and expressing the displacement of Moiré fringes at a point P of FIG. 5B by f·a, the distance between adjacent ones of Moiré fringes corresponds to a phase shift of $2\pi$ as has been mentioned. Therefore, the displacement a of Moiré fringes corresponds to a phase shift of $2\pi$. Accordingly, the phase shift at point P is $2\pi f$.

The phase shift $\phi$ at positions of the Moiré fringes of FIG. 5B can be determined in the above manner. Further, the phase shift $\phi$ at positions between adjacent ones of Moiré fringes can be determined from the phase shift at the positions of Moiré fringes by the interpolation method, or can be determined by a method mentioned below.

More particularly, the wedge-shaped phase shifter shown in FIG. 3 is placed in the propagation path so as to be movable in a direction traversing or perpendicular to the propagation path so that the length of transmission of the phase shifter by the X-ray beam is changeable (FIG. 4). Now, let us consider a case where the phase shifter 19 is moved a distance $\Delta t$.

Figure 5C:
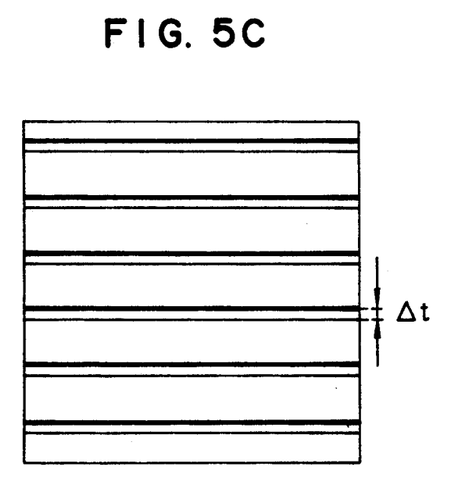
Figure 5D:
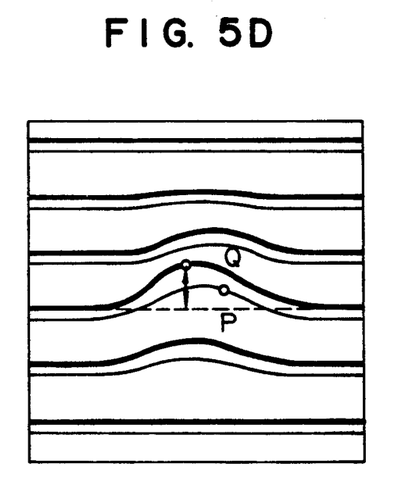

FIGS. 5C and 5D show changes of Moiré fringes in this case. In more detail, FIG. 5C shows the change of Moiré fringes in a case where the object 10 is absent, and FIG. 5D shows the change of Moiré fringes in a case where the object 10 is placed on the propagation path for the signal wave beam. In FIGS. 5C and 5D, thin lines indicate Moiré fringes obtained before the phase shifter 19 is moved, which are identical with FIGS. 5A and 5B. When the phase shifter 19 is moved as mentioned above, the Moiré fringes move by a distance $\Delta t$. Thus, one of the Moiré fringes passes through, for example, a point Q of FIG. 5D, and the phase shift at the point Q is determined. By changing the distance $\Delta t$ from 0 to a, the phase shift $\phi(y, z)$ can be studied in detail. By repeating the above operation each time the object 10 is rotated through a predetermined constant angle, a tomogram of the object 10 can be obtained.

Figure 6:
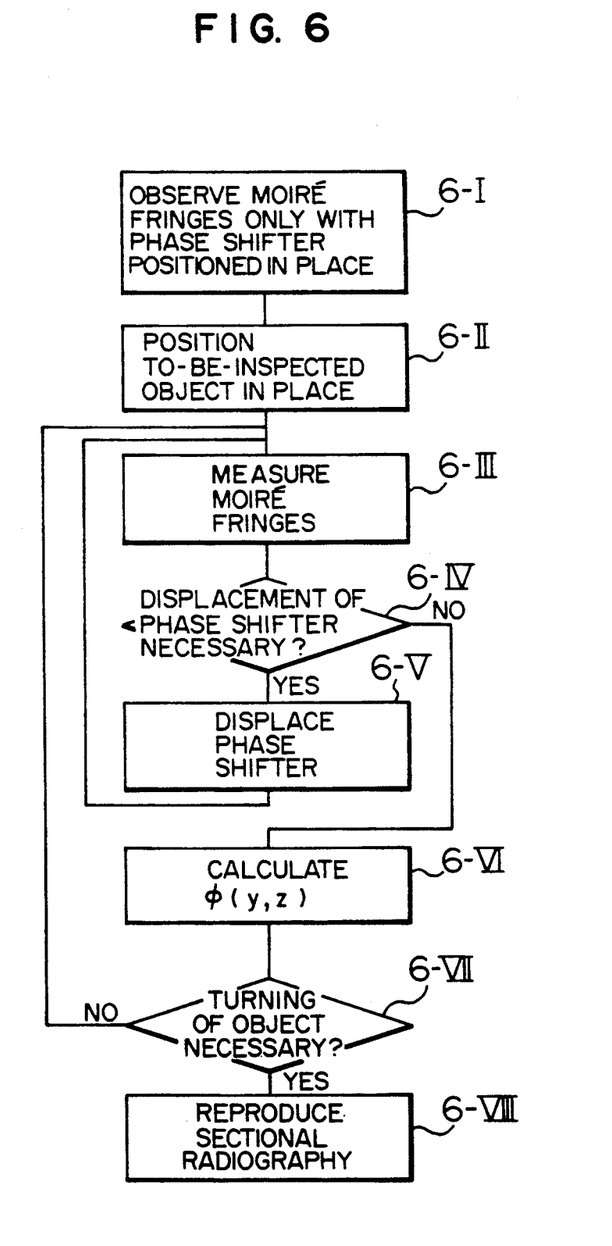
FIG. 6 is a flow chart showing steps for obtaining a tomogram with the apparatus shown in FIG. 3.

FIG. 6 shows processing carried out by the second embodiment, for obtaining a tomogram.

In step 6-I, the phase shifter 19 is placed in one of the propagation paths in the absence of the object 10, and Moiré fringes are observed.

Then, the to-be-inspected object 10 is set (step 6-II), and then Moiré fringes are observed (Step 6-III).

The phase shifter 19 is moved in a direction traversing the propagation path so that the distance the beam transmits through the phase shifter (wedge) in the propagation path direction is varied (step 6-V). The processing in the steps 6-III and 6-V is repeated a plurality of times. For example, in a case where $\Delta t$ is made equal to $a/10$, the above processing is repeated ten times.

The phase-shift distribution $\phi(y, z)$ is calculated on the basis of data obtained in the above steps for interpolation of values of $\phi$ (step 6-VI).

The processing in the steps 6-III to 6-VI is repeated each time the object 10 is rotated about an axis 13 through a predetermined constant angle (for example, 1°), untill the object 10 is rotated through an angle of 180°, and the phase-shift distribution $\phi(y, z)$ is determined at each rotational position of the object, that is, in each of the different projective directions.

Data $\phi(y, z)$ obtained in the above steps is sent to the tomography signal processor 30, to reconstruct a tomogram of the object 10, and the tomogram is displayed on the display screen of the display device 40 (step 18). The controller 41 control operations of the signal converter 31, motor driver 53 and motor driver 55. The controller 41, the signal converter 31 and the tomography signal processor 30 may be realized by an image processor such as the "Medical Purpose Image Processor 68000 System" manufactured by Hitachi Medical Corporation. This system is provided with a 30 Mbyte memory.

EMBODIMENT III

Figure 7:
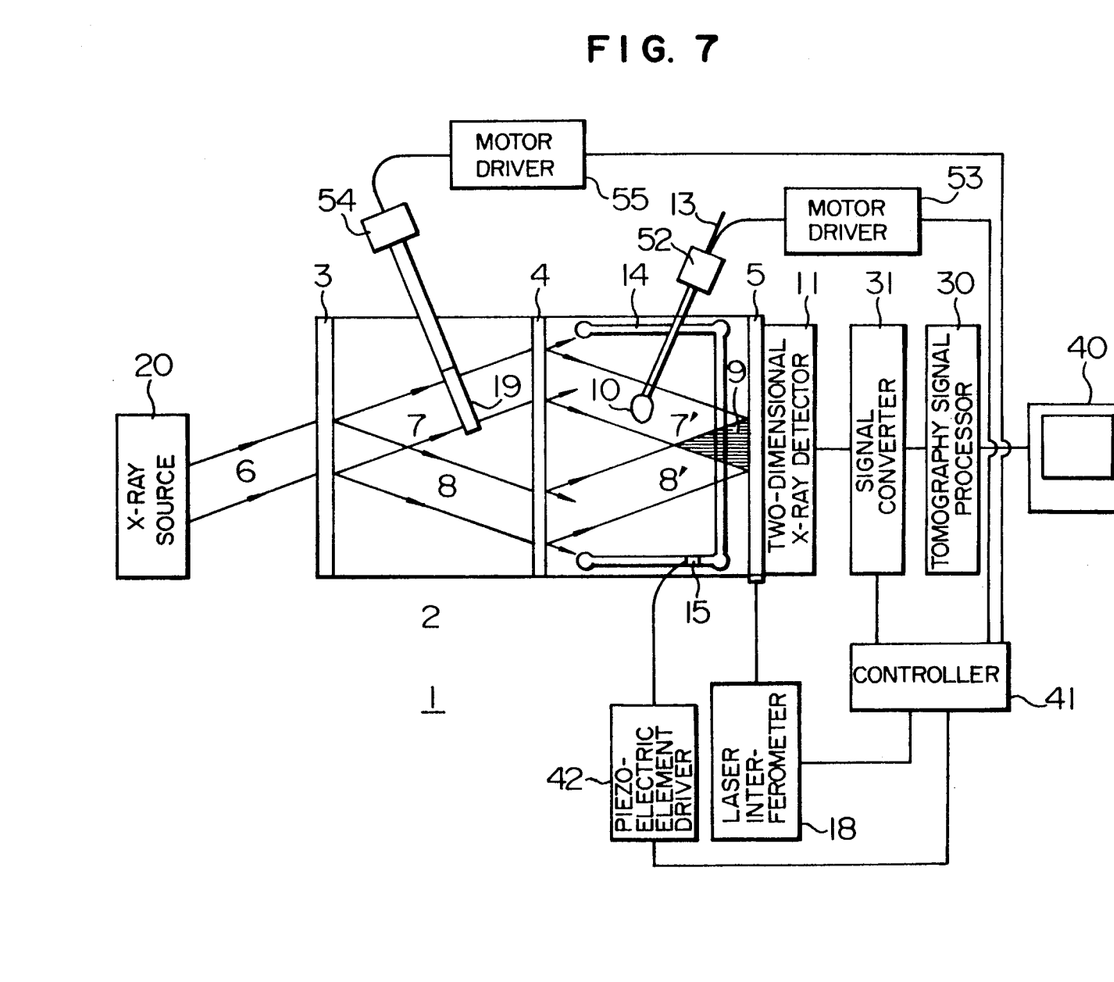
FIG. 7 is a schematic diagram of a tomograph according to another embodiment of the present invention.

Although the phase shifter is moved in the second embodiment, the analyzer may be moved, in place of the phase shifter. FIG. 7 shows an interferometer which is formed so that the analyzer 5 is movable. Referring to FIG. 7, a cut 14 is formed in the base portion 2 of the interferometer so as to reach the back surface of the base portion 2, and thus the analyzer 5 can move in a direction of the diffraction vector (e.g., <110> direction). The analyzer 5 is moved by applying a voltage from a piezoelectric element driver 42 to a piezoelectric element 15 which is set in the cut 14.

Before the analyzer 5 is moved, Moiré fringes appear at positions satisfying an equation $\phi(y, z)=2n\pi$ (where n is an integer). When the analyzer 5 is moved by a distance $\Delta y$, the Moiré fringes are shifted to positions satisfying an equation $\phi(y, z)=2\pi(n+\Delta y/d_{220})$. Accordingly, by changing the displacement $\Delta y$ in a range from zero to $d_{220}$, the phase-shift distribution $\phi(y, z)$ can be studied in detail. The displacement $\Delta y$ of the analyzer 5 can be monitored by two methods. In one of the methods, a mirror 16 is attached to the analyzer 5, and the displacement $\Delta y$ of the mirror 16 is measured directly by a laser interferometer 18 in terms of laser light 17. In the other method, the intensity of X-rays having passed through the analyzer 5 is measured at an off-position of the image of the object. In this case, the intensity of transmitted X-rays varies sinusoidally with the displacement $\Delta y$, and the period of the sinusoidal variation is $d_{220}$. Accordingly, the displacement $\Delta y$ can be determined from the variation of the intensity of transmitted X-rays. Other processing carried out by the embodiment of FIG. 7 is the same as that carried out by the second embodiment.

The controller 41 controls operations of the signal converter 31, laser interferometer 18, piezoelectric element driver 42, motor driver 53 and motor driver 55.

We claim:

1. A phase-contrast tomograph in which an object is irradiated with a radiation beam in a plurality of different directions, to reconstruct a tomograph of the object from images of the object formed of a transmitted beam, each of the images of the object indicates a distribution of a phase shift of a beam having transmitted through the object, wherein the distribution of the phase shift is obtained by using an interferometer.

2. A phase-contrast tomograph according to claim 1, wherein the radiation beam is one of an X-ray beam, a $\gamma$-ray beam and a neutron beam.

3. A phase-contrast tomograph according to claim 1, wherein the interferometer is a Bonse-Hart interferometer.

4. A phase-contrast tomograph according to claim 3, wherein the images of the object formed by irradiating the object with the radiation beam in a plurality of different directions are obtained in such a manner that a radiation-beam source is fixed and the object is rotated about a predetermined axis of rotation, and the axis of rotation is substantially perpendicular to the propagation path for the radiation beam and is substantially parallel to the plane which is parallel both to a signal beam to be transmitted through the object and a reference beam that does not transmit through the object.

5. A phase-contrast tomograph according to claim 3, wherein a reference beam generated in the Bonse-Hart interferometer is selectively blocked by a shutter.

6. A phase-contrast tomograph according to claim 3, wherein a phase shifter is placed on a propagation path for at least one of a signal beam and a reference beam which are both generated in the Bonse-Hart interferometer.

7. A phase-contrast tomograph according to claim 3, wherein an analyzer which is a portion of the Bonse-Hart interferometer, is relatively movable with respect to the other part of the Bonse-Hart interferometer.

8. A tomograph of the type using phase information, comprising:
a radiation beam source for producing a radiation beam;
means for splitting said beam into first and second diffracted beams;
means for establishing first and second paths for said first and second diffracted beams intersecting each other, said establishing means being arranged to receive said first and second diffracted beams;
means for holding a to-be-inspected object on one of said first and second paths so that the diffracted beam propagating along said one path and transmitting through said object produces a signal wave beam while the other diffracted beam produces a reference beam, and interference fringes are generated in a space where said intersection takes place;
means arranged to be located in said space for producing Moiré fringes from said interference fringes; and means coupled to said Moiré fringe producing means for reproducing an image representative of said object.

9. A tomograph according to claim 8, further comprising means for selectively blocking that one of said first and second diffracted beams which forms said reference beam.

10. A tomograph according to claim 8, further comprising means for phase-shifting one of said first and second diffracted beams.

11. A tomograph according to claim 8, further comprising means for displacing said Moiré fringe producing means, and means for determining a displacement of said Moiré fringe producing means.

12. A tomograph according to claim 8, in which said radiation beam is an X-ray beam, a γ-ray beam or a neutron beam.

13. A tomograph according to claim 8, in which said beam splitting means, said path establishing means and said Moiré fringe producing means are constituted by an interferometer.

14. A tomograph according to claim 13, wherein said interferometer is an X-ray interferometer.

* * * * *